United States Patent [19]

Wimmers

[11] Patent Number: Plant 7,485

[45] Date of Patent: Apr. 2, 1991

[54] BOSC PEAR—WIMMERS CULTIVAR

[76] Inventor: Robert L. Wimmers, 2500 Reed Rd., Hood River, Oreg. 97031

[21] Appl. No.: 456,850

[22] Filed: Dec. 21, 1989

[51] Int. Cl.[5] ..... A01H 5/00

[52] U.S. Cl. ..... Plt./36

[58] Field of Search ..... Plt./36

[56] References Cited

U.S. PATENT DOCUMENTS

P.P. 5,243 6/1984 Fukui ..... Plt. 36

*Primary Examiner*—Howard J. Locker

*Attorney, Agent, or Firm*—Burns, Doane, Swecker & Mathis

[57] ABSTRACT

A new and distinct variety of Bosc pear is provided which originated as a whole tree mutation. The fruit of the new variety assumes a uniform russet appearance at least one month earlier than other Bosc pear varieties, and when ripened exhibits a more bronze coloration as illustrated. The fruit of the new variety exhibits small inconspicuous dots on its surface and its surface exhibits a slightly roughened texture. Commonly the fruit is ready for picking approximately one week later than that of the standard Bosc pear variety. Also, the fruit of the new variety when ripened tends to exhibit a higher soluble solids content and tends to be sweeter than that of other Bosc pear varieties.

3 Drawing Sheets

SUMMARY OF THE INVENTION

The new and distinctive variety of the present invention resulted as a whole tree mutation of unknown causation. More specifically, the new variety was discovered by me during 1980 while growing among trees of the standard Bosc pear variety and trees of the Bartlett pear variety in my orchard located at 2500 Reed Road, Hood River, Oreg. The Bosc pear trees which included the tree of my discovery had originally been planted as young whips during about 1970. The standard Bosc pear variety from which the new variety likely was derived sometimes is known as the OP-5 Bosc pear variety and is non-patented in the United States. Such standard Bosc variety is believed to have been selected by scientists at Oregon State University and the United States Department of Agriculture because of its favorable fruit characteristics and freedom from the stony pit virus. Had I not discovered and preserved this new variety, it would have been lost to mankind.

The new variety bears quality pears which (a) assume a uniform russet appearance at least one month earlier than other known Bosc pear varieties, (b) assume an attractive bronze coloration as illustrated when ripened, (c) bear small inconspicuous dots on the fruit surface, (d) exhibit a slightly roughened surface texture, (e) tend to exhibit a higher soluble solids content when ripened than other Bosc pear varieties, (f) tend to be sweeter than other known Bosc pear varieites, and (g) are ready for picking approximately one week later than the standard Bosc pear variety.

The fruit of the new variety has been found to russet much earlier than other Bosc pear selections. For instance, during 1989 a definite russet began to appear on fruit of the new variety on June 2nd. In contrast, the russet on the fruit of the Golden Russet variety of Bosc pear (U.S. Plant Pat. No. 5,243) was not obviously apparent until July, and the russet on the fruit of the standard Bosc pear variety was not obviously apparent until August. The russet on the fruit of the new variety initially appears as a much more solid and complete russet than on other Bosc pear varieties. When one removes the outer surface of the skin of the new variety with a knife soon after the russet coloration appears, a dark green coloration commonly tends to persist under the russet coloration. However, as the fruit of the new variety ripens and as the russet on the fruit surface blends deeper into the skin, such underlying dark green coloration diminishes and is no longer as apparent. The ultimate bronze coloration assumed by the fully ripened fruit of the new variety can be readily distinguished from the more coppery fruit coloration of the Golden Russet variety of Bosc pear (U.S. Plant Pat. No. 5,243).

The fruit surface of the Golden Russet variety of Bosc pear tends to be smooth in contrast to slight roughness to the hand exhibited by the fruit surface of the new variety.

The fruit pressure of the new variety tends to be greater than that of other Bosc pear varieties and tends to provide a firmer fruit at the time of picking. Also, after ripening the fruit of the new variety tends to have a higher concentration of soluble solids and total acids than other Bosc pear varieties.

As with other pear varieties, the time for picking of the fruit of the new variety in the fall is dependent somewhat on the weather conditions which influence the time for blossoming in the spring. Generally, it has been found that the new variety should be picked about one week later than the standard Bosc pear variety (i.e., OP-5 Bosc variety). Optimum harvest times for the new variety at Hood River, Oreg., in recent years have been as follows:

1987—September 14th,
1988—September 27th, and
1989—September 26th.

The original tree of the new variety has been carefully preserved. Additional trees of the new variety have been asexually reproduced at Hood River, Oreg., by topworking onto existing trees, both young and old. The characteristics of the new variety have been confirmed to be stably transmitted in a true-to-type manner through such grafting. Following propagation the fruit formed on the new trees the fruit continues to exhibit the same distinctive characteristics as the original tree.

The new variety has been named the Wimmers cultivar. It is anticipated that trees and fruit of the new variety will be marketed in the United States under the BRONZE BEAUTY trademark.

BRIEF DESCRIPTION OF THE PHOTOGRAPHS

The accompanying photographs show typical specimens of the new variety in color as nearly true as is reasonably possible to make the same in a color illustration of this character. The photographs were obtained at Hood River, Oreg.

FIG. 1 illustrates for comparative purposes typical unripened fruits and foliage of the new variety as they appeared on Aug. 18, 1989 together with a single fruit of the standard Bosc pear variety. The fruits of the new variety are present on the right and on the left and a single fruit of the standard Bosc pear variety is present at the center. It will be observed that the fruit of the new variety, unlike that of the standard Bosc pear variety, has already begun to assume a russet appearance.

Figure 1:
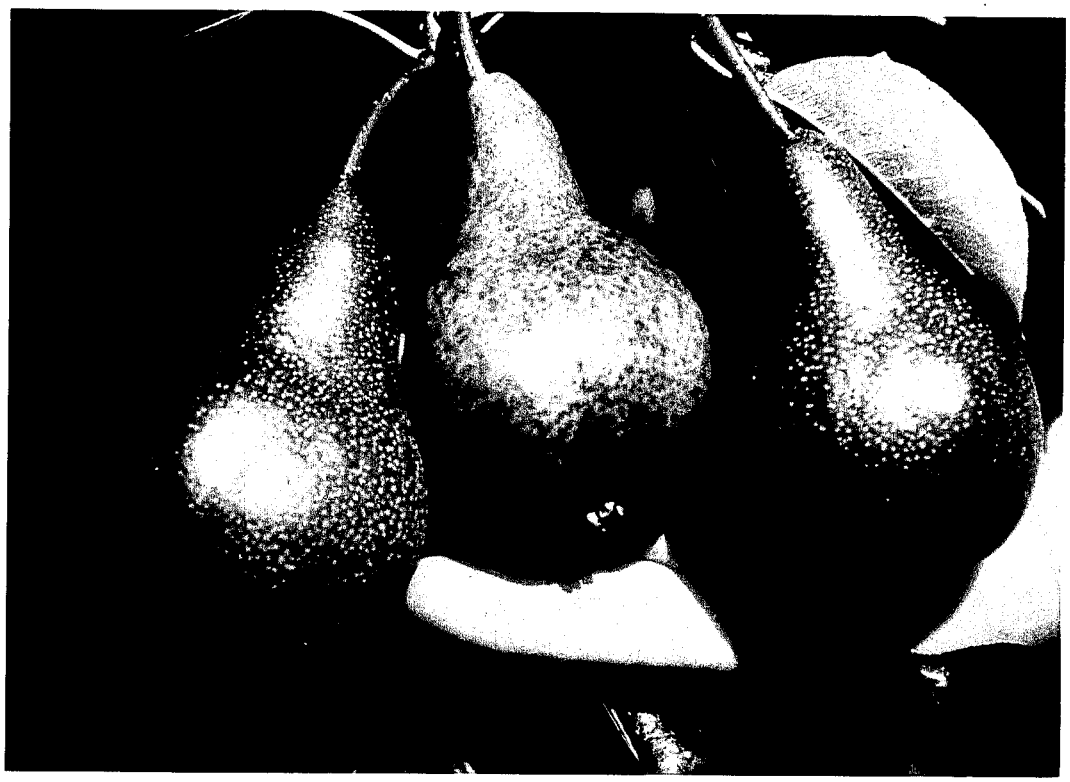
Figure 2:
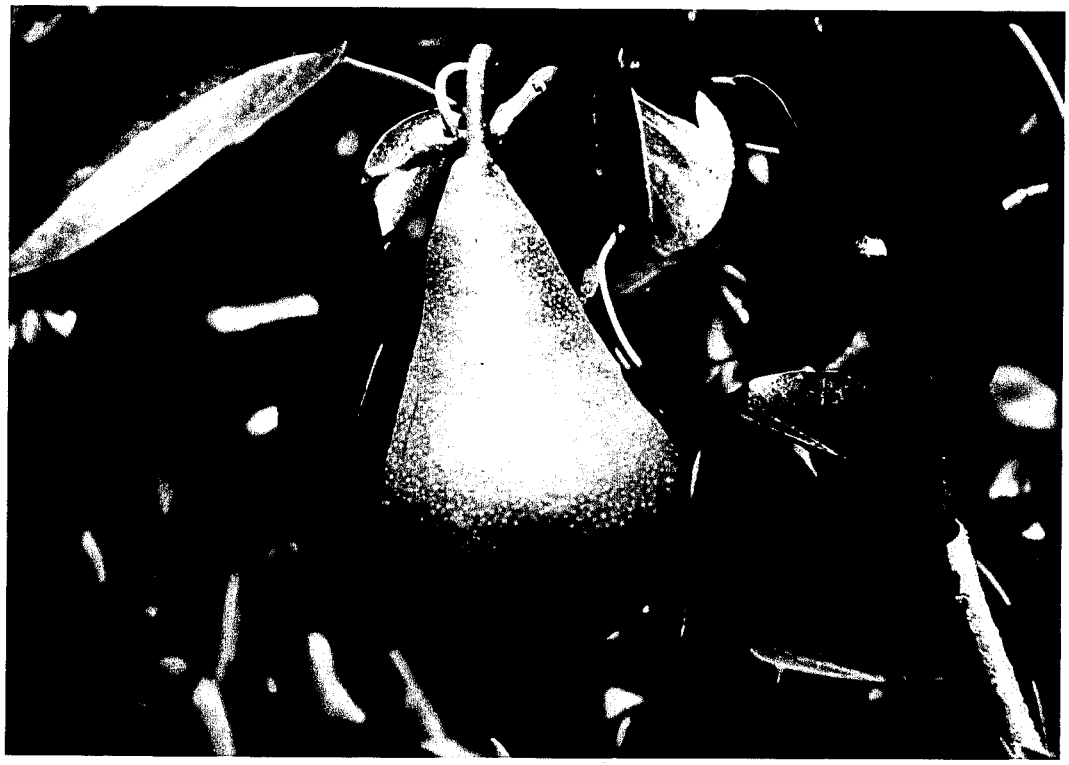
FIG. 2 illustrates a representative unripened fruit and foliage of the new variety as they appeared later in the growing season on Sept. 5, 1989. It will be observed that the russet coloration of the fruit has further intensified.
Figure 4:
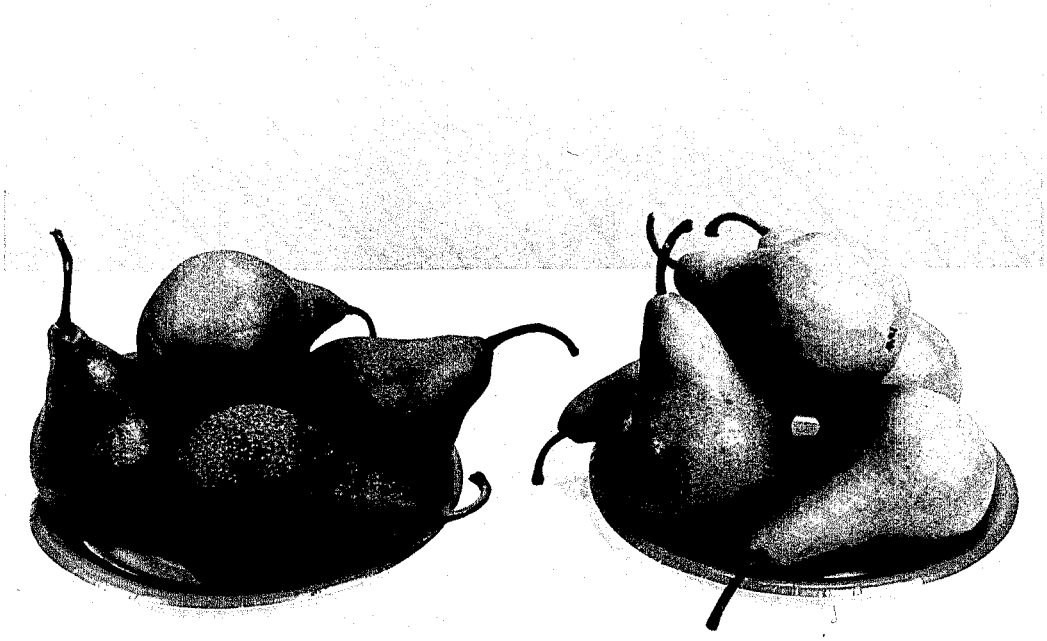

FIG. 4 illustrates for comparative purposes typical fruits of the new variety and the Golden Russet variety of Bosc pear (U.S. Plant Pat. No. 5,243) on approximately Nov. 20, 1989 following cold storage and further ripening. Such fruits are ready to eat. The fruits of the new variety are on the left and the fruits of the Golden Russet variety of Bosc pear are on the right. It will be observed that the new variety exhibits a bronze coloration and the fruits of the Golden Russet variety of Bosc pear exhibit a more coppery coloration.

Figure 5:
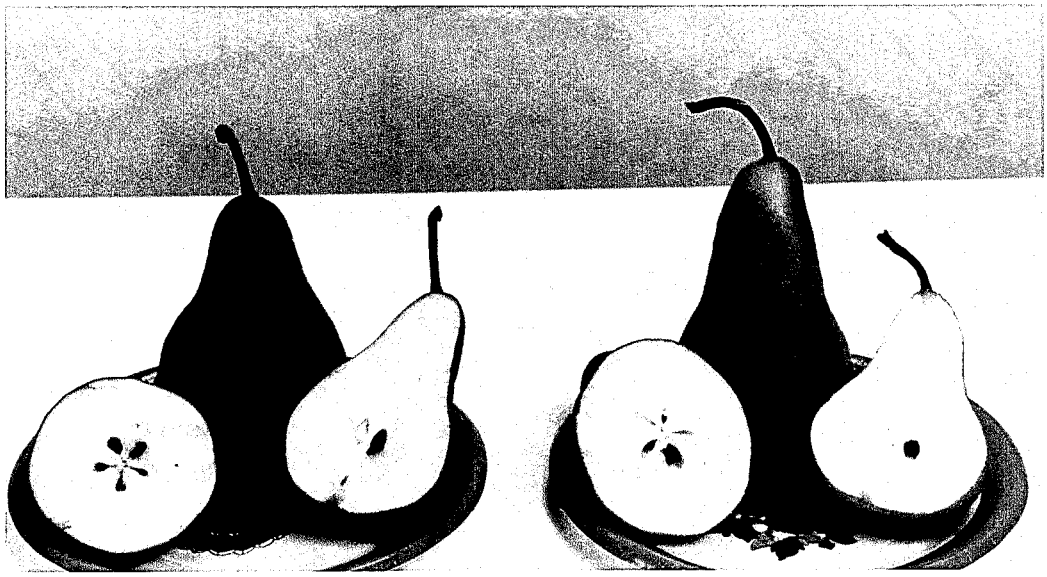
Figure 3:
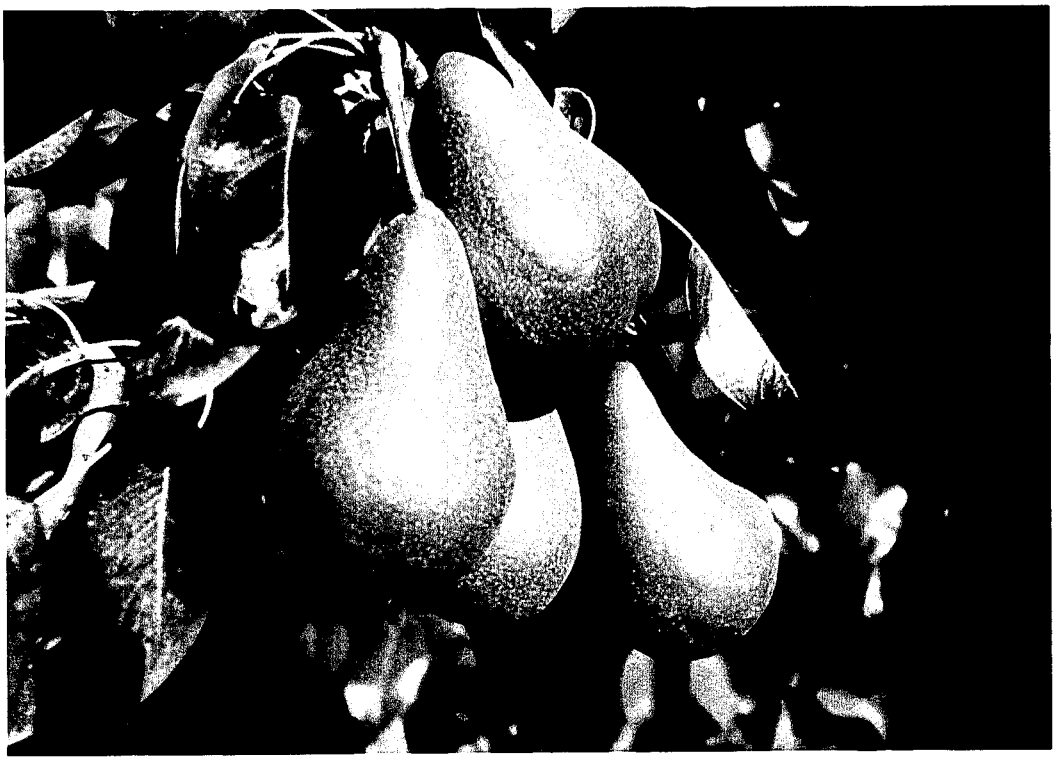
FIG. 3 illustrates a cluster of representative fruits and foliage of the new variety at harvest time (i.e., on Sept. 27, 1989). The attractive bronze coloration of the fruit is apparent.

FIG. 5 illustrates for comparative purposes typical fruits of the new variety and the Golden Russet variety of Bosc pear while whole and in longitudinal and transverse cross-sections on approximately Nov. 20, 1989 following cold storage and further ripening. Such fruits are ready to eat. The fruits of the new variety are on the left and the fruits of the Golden Russet variety of Bosc pear are on the right. Once again the bronze coloration of the new variety vs. the more coppery coloration of the Golden Russet variety of Bosc pear is apparent.

DETAILED DESCRIPTION

The following is a detailed description of the new variety's characteristics as observed at Hood River, Oreg. The color terminology is in accordance with the *Munsell Book of Color* except where general color terms of ordinary dictionary significance are used.

Tree:
- *Size.*—Medium to large.
- *Vigor.*—Similar to standard Bosc pear variety.
- *Form.*—Upright and spreading.
- *Growth.*—Moderate.
- *Hardiness.*—Similar to standard Bosc pear variety, moderately large.
- *Production.*—Very productive.
- *Bearing.*—Late, somewhat regular bearer.

Trunk:
- *Form.*—Straight.
- *Size.*—Stocky.
- *Texture.*—Medium smooth.

Branches:
- *Main branches.*—Stocky, spreading, thick, and strong.
- *Lateral branches.*—Spreading, smooth, medium thick, and covered with gray skin.
- *Branchlets.*—Glossy-brown, smooth, and glabrous.
- *Lenticels.*—Large, raised, and obvious.

Leaves:
- *Size.*—Medium, average length approximately 7.87 cm. (approximately 3.09 inches), and average width approximately 5.18 cm. (approximately 2.04 inches).
- *Form.*—Ovate.
- *Apex.*—Taper-pointed.
- *Thickness.*—Medium-thick.
- *Pubescence.*—None.
- *Texture.*—Smooth, leathery.
- *Margin.*—Finely serrate, toothed.
- *Petiole.*—Slender, medium-thick, average length approximately 3.85 cm. (approximately 1.51 inch).
- *Color.*—Upper surface is medium green, 7.5 gy 3/4, and under surface is lighter green, 5 gy 6/4.
- *Leaf-buds.*—Form is obtuse, pointed, and appressed.
- *Leaf-scars.*—Prominent.

Flowers:
- *Size.*—Large.
- *Color.*—White and showy.
- *Petals.*—Obovate and broad.
- *Pedicels.*—Light green.
- *Fertility.*—Fertile, but requires cross-pollination for good crop and good fruit size.
- *Buds.*—Large, pointed and conical.

Fruit:
- *Date of first picking.*—Sept. 20th in 1989.
- *Date of last picking.*—Sept. 30th in 1989.
- *Retention.*—Like all Bosc pear varieties is subject to drop.
- *Size.*—Large, average length is approximately 10.1 cm. (approximately 3.9 inches) and average width is approximately 6.78 cm. (approximately 2.7 inches).
- *Form.*—Acute, ovate, pyriform, and has long and tapered neck as illustrated.
- *Stem.*—Curved, slender, and average in length.
- *Color.*—Bronze brown overall, 2.5 y 4/4, at harvest.
- *Cavity.*—Obtuse or lacking, shallow and narrow, and russeted.
- *Calyx.*—Small and open.
- *Lobes.*—Persistent, short, broad, and obtuse.
- *Basin.*—Shallow, narrow, obtuse, smooth, and russeted.

Skin:
- *Texture.*—Granular.
- *Color.*—Overall bronze-tinted unbroken heavy russet surface, 2.5 y 4/4 at harvest with no yellow or green ground color, and 7.5 yr 5/8 after ripening. Lacks uneven patch effect of the standard Bosc pear variety (i.e., OP-5 Bosc pear variety).
- *Dots.*—Small and inconspicuous.

Flesh:
- *Color.*—2.5 gy 9/2 at harvest and 7.5 y 9/2 after ripening.

*Texture.*—Juicy, buttery, melting, and slightly granular.

*Flavor.*—Excellent.

*Eating quality.*—Excellent, delicious when properly ripened.

*Core.*—Large, elliptical, clasping corelines, bluntly pointed at calyx end, long pointed at stem end, and fleshy between seeds.

*Calyx tube.*—Short, wide, and conical.

*Seed.*—Short and obtuse.

*Color.*—Dark Brown, 7.5 y 9/2, and 7.5 yr 2/4 after ripening.

Use: Fresh market, dessert, shipping.

Keeping quality: Best.

Shipping quality: Best.

Resistance to insects and diseases: Similar to the standard Bosc pear variety (i.e., OP-5 Bosc pear variety), resistant to scab and mildew, subject to fire blight, and medium resistance to psylla and mites.

The fruit of the new variety exhibits a distinctive solid and heavy overall bronze appearance. This uniform russet appears at least one month prior to the formation of russet on other Bosc pear varieties. The russet on the fruit of the new variety becomes less dominant as the fruit ripens and then becomes well blended with the fruit's overall appearance.

When representative fruits of the new variety and of the standard Bosc pear variety (i.e., OP-5 Bosc pear variety) harvested in 1987 were tested for firmness, soluble solids content, and total acid content, the values reported in TABLE I were obtained.

TABLE I

| | Firmness (pounds) | Soluble Solids Content (percent) | Total Acid Content (meq.) |
|---|---|---|---|
| At Harvest September 14, 1987 | | | |
| Wimmers Cultivar | 13.3 | 13.6 | 3.1 |
| OP-5 Bosc Pear Variety | 12.1 | 11.6 | 2.2 |
| After 3 Months Cold Storage and Before Ripening | | | |
| Wimmers Cultivar | 11.7 | 16.1 | 3.0 |
| OP-5 Bosc Pear Variety | 9.2 | 14.2 | 1.6 |
| After 3 Months Cold Storage and After Ripening | | | |
| Wimmers Cultivar | 3.4 | 15.9 | 2.4 |
| OP-5 Bosc Pear Variety | 4.6 | 14.2 | 1.7 |

When representative fruits of the new variety and of the standard Bosc pear variety (i.e., OP-5 Bosc pear variety) harvested in 1988 were tested for firmness, extractable juices, soluble solids content, and total acid content, the average values reported in TABLE II were obtained.

TABLE II

| | Firmness (pounds) | Extractable Juices (meq.) | Soluble Solids Content (percent) | Total Acid Content (meq.) |
|---|---|---|---|---|
| After Cold Storage and 1 Day @ 20° C. December 5, 1988 | | | | |
| Wimmers Cultivar | 14.69 | 59.3 | 15.23 | 2.49 |
| OP-5 Bosc Pear Variety | 12.27 | 64.8 | 12.77 | 1.71 |

TABLE II-continued

| | Firmness (pounds) | Extractable Juices (meq.) | Soluble Solids Content (percent) | Total Acid Content (meq.) |
|---|---|---|---|---|
| After Cold Storage and 7 Days @ 20° C. December 7, 1988 | | | | |
| Wimmers Cultivar | 4.14 | 69.0 | 14.67 | 2.66 |
| OP-5 Bosc Pear Variety | 4.36 | 71.6 | 12.7 | 1.62 |

When representative fruits of the new variety and of the standard Bosc pear variety (i.e., OP-5 Bosc pear variety) from the 1988 and 1989 harvests were analyzed for firmness on various days during the growing season, the values reported in TABLE III were obtained.

TABLE III

| | Wimmers Cultivar Firmness (pounds) | OP-5 Bosc Pear Variety Firmness (pounds) |
|---|---|---|
| 1988 | | |
| September 11th | 17.4 | 16.3 |
| September 17th | 16.5 | 15.0 |
| September 27th | 13.6 | 12.2 |
| 1989 | | |
| September 7th | 15.9 | 14.6 |
| September 15th | 15.7 | 14.0 |
| September 20th | 14.5 | 13.0* |
| September 26th | 14.1* | — |

* = Harvested

When representative fruits of the new variety and of the Golden Russet variety of Bosc pear (U.S. Plant Pat. No. 5,243) harvested in 1989 were tested for firmness, extractable juices, soluble solid content, and total acid content, the average values reported in TABLE IV were obtained.

TABLE IV

| | Firmness (pounds) | Extractable Juices (meq.) | Soluble Solids Content (percent) | Total Acids Content (meq.) |
|---|---|---|---|---|
| On October 12, 1989 After Harvest on September 26, 1989 and Cold Storage | | | | |
| Wimmers Cultivar | 14.1 | 66.8 | 15.03 | 3.06 |
| Golden Russet Variety | 13.5 | 71.7 | 14.67 | 3.32 |
| On October 20, 1989 After Harvest on September 26, 1989, Cold Storage and 7 days at 68° F. | | | | |
| Wimmers Cultivar | 3.10 | 54.8 | 15.8 | 3.18 |
| Golden Russet Variety | 2.58 | 57.6 | 14.7 | 3.11 |

Accordingly, the fruit of the new variety when subjected to cold storage and ripening has been shown to exhibit highly attractive analytical values.

I claim:

1. A new and distinct variety of pear tree which is believed to be a whole tree mutation of the standard Bosc pear variety, substantially as illustrated and described, capable of forming quality fruit which (a) assumes a uniform russet appearance at least one month earlier than other known Bosc pear varieties, (b) assumes an attractive bronze coloration when ripened, (c) bears small inconspicuous dots on the fruit surface, (d) exhibits a slightly roughened surface texture, (e) tends to exhibit a higher soluble solids content when ripened than other known Bosc pear varieties, (f) tends to be sweeter than other known Bosc pear varieties, and (g) is ready for picking approximately one week later than the standard Bosc pear variety.

* * * * *